United States Patent [19]

May

[11] Patent Number: 6,156,271
[45] Date of Patent: Dec. 5, 2000

[54] ASSAY DEVICES

[75] Inventor: Keith May, Bedford, United Kingdom

[73] Assignee: Unilever Patent Holdings B.V., Vlaardingen, Netherlands

[21] Appl. No.: 09/025,108

[22] Filed: Feb. 17, 1998

[30] Foreign Application Priority Data

Feb. 14, 1997 [GB] United Kingdom .................... 9703094

[51] Int. Cl.[7] .................................................. G01N 33/48
[52] U.S. Cl. .............................. 422/58; 422/61; 436/169; 436/177; 436/178
[58] Field of Search ................................. 422/56, 58, 61; 436/169, 175, 177–178, 808, 814, 906

[56] References Cited

U.S. PATENT DOCUMENTS

| | | | |
|---|---|---|---|
| 4,790,640 | 12/1988 | Nason | 422/58 |
| 5,467,778 | 11/1995 | Catt et al. | 422/58 |
| 5,504,013 | 4/1996 | Senior | 422/56 |
| 5,556,789 | 9/1996 | Graw et al. | 422/58 |
| 5,622,871 | 4/1997 | May | 422/58 |

*Primary Examiner*—Lyle A. Alexander
*Attorney, Agent, or Firm*—Pillsbury Madison & Sutro LLP

[57] ABSTRACT

An assay device incorporates a composite strip comprising at least two bodies of porous liquid-conductive material in liquid-flow contact with each other via an interface and together defining at least part of a liquid flow path through which liquid must flow during the performance of an assay, wherein at said interface the lateral dimension, relative to the direction of the liquid flow path, of the contact area of the upstream body is narrowed such that liquid flow from the upstream body into the downstream body is focused towards the centre-line of the flow path in the downstream body, thereby reducing the likelihood that liquid will deviate from the intended flow path. The upstream body can be a sample-collecting wick, terminating at the interface as a point or prow (FIG. 7).

14 Claims, 3 Drawing Sheets

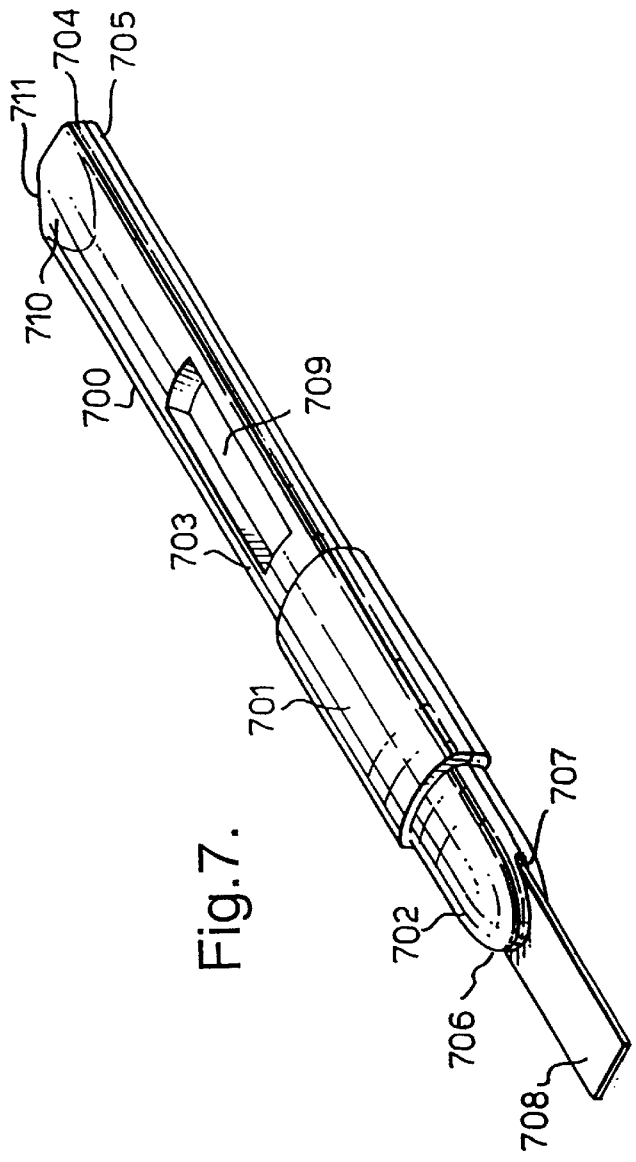
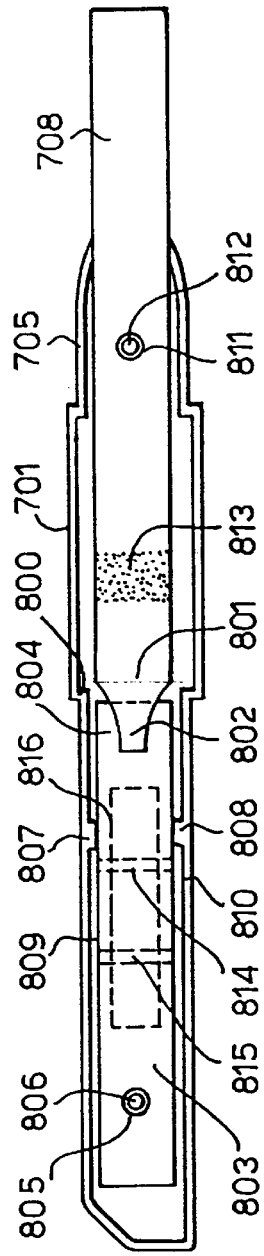

ASSAY DEVICES

FIELD OF THE INVENTION

This invention relates to assay devices and particularly to such devices wherein liquid travels along a flow path within porous material.

BACKGROUND TO THE INVENTION

Many simple and convenient assay device s are now available which comprise a strip or sheet of porous material through which sample liquid progresses and carries a labelled specific binding re agent into a test zone in which the assay result is revealed. Such devices are loosely referred to as "immunochromatographic" devices, although the specific binding reagent t may not necessarily be immunochemical in the strictest sense. Examples of such devices are described in EP 186799, EP 291194 and EP 383619.

In a typical device the sample liquid is applied to one end of a defined liquid flow path. Usually the sample liquid is received by a physically distinct body of porous material, and during the course of the assay must flow from this first body into one or more other porous bodies arranged in series. Usually the successive porous bodies have different characteristics, such as porosity or composition. Usually, in order for the assay to work efficiently, there should be unimpeded flow of sample liquid from one body into the next. Typically the porous bodies are contained, wholly or partially, within a protective casing constructed for example from plastics material. Inevitably there is at least partial contact between one or more inner surfaces of the casing and one or more of the porous bodies. The series of porous bodies can be firmly linked to one another by being fixed to a common support, for example by being laminated onto a single backing strip. Alternatively, adjoining bodies can be held in appropriate contact merely by being constrained within the casing.

Usually the sample liquid flows through the device by capillary action. The intention is that the porous nature of the strip components ensures that the liquid flows only through these components and not elsewhere within the device. However, in a typical device, especially one which has a protective casing, there may be opportunities for the liquid to find alternative flow paths created, for example, by close proximity between an inner surface of the casing and the exterior of one of the porous components. This tendency to deviate from an intended flow path may be exacerbated if a user of the device applies too great a volume of sample to the device. Under such circumstances the device may tend to "flood". Such flooding may cause a significant proportion of the sample liquid within the device to bypass a critical stage in the intended flow path. For example, some of the liquid may reach a test zone without encountering one or more reagents, such as a mobilisable labelled reagent, that have been placed deliberately in the intended flow path. Flooding may therefore lead to a false assay result, or at least lead to a loss of assay sensitivity.

An objective of the present invention is to provide assay devices in which the likelihood of sample liquid deviating from an intended flow path is reduced.

GENERAL DESCRIPTION OF THE INVENTION

The invention provides an assay device incorporating a composite strip comprising at least two bodies of porous liquid-conductive material in liquid-flow contact with each other via an interface and together defining at least part of a liquid flow path through which liquid must flow during the performance of an assay, wherein at said interface the lateral dimension, relative to the direction of the liquid flow path, of the contact area of the upstream body is narrowed such that liquid flow from the upstream body into the downstream body is focused towards the centre-line of the flow path in the downstream body. Preferably the narrowed portion of the upstream body forms a point or prow. The upstream body can be a sample receiving member or wick.

The bodies of porous material can be contained at least partially within a hollow casing constructed of solid moisture-impervious material. Generally an inner surface of the casing being in contact with or closely adjacent to the bodies of porous material at their interface. In one embodiment the bodies of porous material are physically separate components and are held in contact with one another solely by being constrained within the hollow casing.

The bodies of porous material can be physically separate components and are placed in contact with one another during assembly of the device. Alternatively they may be fixed in contact with each other, e.g. by being laminated onto a common backing material.

Preferably the bodies of porous material are contained at least partially within a hollow casing constructed of solid moisture-impervious material, and the sample receiving member or wick protrudes from the casing but the portion of the sample receiving member or wick which is narrowed is within the casing.

In one embodiment, the upstream body incorporates a mobilisable reagent upstream from the narrowed portion of the porous body. Desirably, where the device comprises a casing, the mobilisable reagent is on a portion of the body protected within the casing.

A further aspect of the invention is a wick for use as part of an assay device, which wick comprises a strip of porous material having at one end thereof a narrowed point or prow centred on the longitudinal axis of the strip. Preferably the narrowed portion comprises not more than 35% of the overall length of the wick. Preferably at the point or prow, the width of the strip is narrowed by at least 50%. Ideal wick materials are non-woven fabric, and fibrous plastics.

The materials from which the various porous components in the assay device are made are not critical to the present invention. Any of the porous materials conventionally used in devices of this type can be employed. A wide range of porous materials are used successfully. These include conventional cellulosic papers and nitrocellulose. Glass fibre materials and polyethylene frit are often used for porous bodies which provide the initial location of mobilisable labelled reagents. The sample receiving member can also be made from such materials. Ideal materials for the sample receiving member are fibrous plastics materials such as "Porex", and non-woven fabrics as described in more detail below. Where necessary, such materials can be rendered appropriately hydrophilic by treatment with surface active agents, for example. Deposition of reagents onto any of these materials to provide the assay chemistry can be accomplished by any of the techniques now standard in the art. The specific binding mechanisms by which such assays function can be entirely conventional. Typically such assays involve antibody/analyte reactions of either a sandwich or competitive format. If desired, the creation of a complex, including a labelled reagent to reveal the assay result, can be accomplished with the aid of indirect binding or capture mechanisms, for example, using specific binding pairs such as avidin and biotin. The choice of such routine matters does not influence the liquid flow focussing concept that is fundamental to the invention.

In a preferred context, the invention is applied in assay devices are designed to be "self-sampling" so that the user merely needs to contact the device with a liquid sample such as a body fluid in order to initiate the assay procedure. In many such devices this is the only action that the user needs to perform before the result of the assay becomes visible or readable. Many of such devices are based on the principle of "immunochromatography". The device contains a strip of porous carrier material along which the applied liquid sample can move. While such movement is occurring, one or more reagents within the device are carried into a detection zone on the strip and cause the assay result to be revealed. Commonly, a labelled material is mobile within the strip when moist and the binding of this labelled material in the detection zone provides the means whereby the assay result becomes readable. Examples of such self-sampling devices are described in EP 291 194 and EP 383 619.

The self-sampling facility can be provided by means of a bibulous sample receiving member or "wick". The material from which the wick is made is chosen such that applied liquid is absorbed very rapidly into the wick. The wick then acts as a reservoir of sample liquid which feeds progressively into the porous strip to drive the immunochromatographic process. The mobile labelled reagent may be incorporated in the strip itself or elsewhere within the device, upstream from the detection zone. In EP 291 194 it is suggested that the labelled reagent can be incorporated in the wick. Ideal labelled reagents useful in these assay devices are reagents (generally specific binding reagents) labelled directly or indirectly with water-insoluble particulate direct labels such as dye sols, metallic (eg. gold) sols, non-metallic elemental particles such as selenium and carbon, and other minute coloured particles such as coloured latex (polystyrene) particles and dye-filled liposomes, all known per se for this purpose.

In accordance with WO96/09546 the wick can comprise non-woven fabric. Preferred non-woven material is made by the process known as hydroentanglement. Ideally no chemical treatment or chemical curing is used during the manufacturing process. Such materials are already known per se and are widely used to make cleaning cloths and wipes. The non-woven wick material is preferably hydrophillic. If the overall character of the fabric is hydrophobic, it can be treated for example with surface active agent to render it hydrophillic in use. It can be made from a blend of fibres. This blend can be a mixture of hydrophobic fibres and hydrophillic fibres, but the overall character of the material is preferably hydrophillic. An ideal blend comprises a mixture of viscose and polyester e.g. about 30% viscose and about 70% polyester. However, single-component fabrics, such as 100% viscose, can be used. The "weight" of the non-woven material is important. The weight of the material is preferably at least about 50 g/m$^2$, and more preferably at least about 70 g/m$^2$. Generally it is not necessary for the weight to exceed about 120 g/m$^2$. Use of a wick made from non-woven fabric material can provide much improved wicking properties and very efficient release of any dried labelled reagent which may be incorporated in the wick.

Although such fabric materials are conventionally described as being "non-woven", this does not necessarily mean that the fibres that make up such fabric are arranged in a totally random manner. It is generally found, as a result of the process by which the fabric is made, that a distinct proportion of the fibres lie predominately in one direction and that the remainder lie predominately in a direction at right angles to the first direction. The wick material, if fibrous such as non-woven fabric, is preferably selected and arranged such that the majority of the fibres lie parallel to the direction in which liquid should flow along the wick into the device. Preferably, the numerical ratio of flow-parallel fibres to flow-orthogonal fibres should be about 2:1 or greater, provided that there are sufficient flow-orthogonal fibres present to maintain the mechanical integrity of the non-woven material for manufacturing purposes.

Preferably the wick comprises only a single sheet or layer of the non-woven fabric. This considerably facilitates manufacture and quality control of an assay device when the wick is used to contain one or more reagents important to the assay chemistry, such as a mobile labelled reagent. If the wick is constructed of multiple layers of bibulous material, it is difficult to ensure that the reagent(s) are deposited consistently in the wick during manufacture, and flow of sample liquid through the multi-layer structure may be uneven, and lead to inefficient or variable uptake of the reagent(s).

In order to constitute an effective wick when used in an immunochromatographic assay device, the wick should have sufficient absorptive capacity. The wick liquid capacity should exceed the capacity of the strip (together with any sink at the distal end of the strip, if provided).

Preferably, where the wick material is in thin sheet form, such as the non-woven fabric, layer is bonded to a supporting layer of non-water-absorbent material, such as plastics sheet. Polyester sheet is ideal. Bonding can readily be achieved using a variety of adhesives, known per se in the lamination art, the adhesion step being induced by pressure, heat or the use of two-component adhesives.

It is self-evident that the quantity and nature of the adhesive should not significantly impair the absorbency and flow properties of the non-woven fabric when bonded to the support. Neither should the adhesive contain any reagents, such as unreacted excess monomers, in amounts that could interfere with the efficiency of the specific binding or other reactions that must occur within the assay device during use.

If desired, the wick can incorporate components that assist the performance of the assay, such as buffering agents and surfactants.

An important context in which devices in accordance with the invention can be applied is home-use testing technology, especially for precise quantitative testing. A convenient example, which is a logical extension of the present consumer interest in home-use pregnancy testing and ovulation prediction testing, is accurate monitoring of the ovulation cycle, not merely to enhance the likelihood of conception but indeed to provide reliable information for the purposes of contraception. Proposals have been made to analyse body fluids with this objective in mind. A common theme is to monitor periodic fluctuations in various hormone metabolite levels in urine. An important example is the determination of any body fluid analyte, especially in the monitoring of the human ovulation cycle by the determination of one or more hormones or metabolites thereof in body fluid, such as urine, for example either luteinizing hormone (LH) and/or estrone-3-glucuronide (E3G). Usually two or more such analytes are measured together to provide sufficient information.

Within this context, an ideal home-use sample liquid testing device includes a porous carrier material, such as a strip, through which applied sample liquid such as urine can permeate and wherein the assay result occurs by means of specific binding of a detectable material in one or more precisely-defined regions (detection zones) of the carrier, such as one or more narrow lines or small dots each containing an immobilized specific binding reagent.

Such devices can be used in conjunction with an electronic device for monitoring the fertility status of the human ovulation cycle and providing a user of said device with an indication of said fertility status, typically comprising:

a) reading means for reading a dual-analyte assay device;

b) information processing means for determining from said reading of said assay device, body fluid sample concentration values for at least two analytes;

c) information processing means and memory means for deriving from said determined concentration values and from previously determined concentration values an indication of the current fertility status of a human subject under test; and d) display means for communicating said current fertility status to said user of said electronic device. Preferably, the device additionally comprises receiving means for receiving said assay device, said reading means being located within said receiving means. Reading is best achieved by optical transmission through said assay device while received by said receiving means. Preferably the display means comprises one or more light sources which provides a coloured signal to said user, a variation in said fertility status being indicated by a colour change. Further details are provided in EP 703454.

This context may rely on the measurement of urinary analytes, such as E3G, LH and pregnanediol-3-glucuronide (P3G). These include monovalent analytes such as haptens. EP 703454 describes improved assays by means of which two or more analytes can be determined simultaneously in the same sample. When an assay is intended to detect the presence and/or amount of just one analyte in a sample liquid, it is relatively easy to configure the assay conditions to achieve this result and to eliminate the effect of other components that may be present in the sample. However, when it is desired to use a single assay device to determine more than one different analyte in the same sample liquid the task of "balancing" the conditions to ensure that the separate assay reactions proceed efficiently and effectively is much more difficult, especially in a strip-format assay.

The flow-focussing wick of the present invention can be applied to advantage in a strip-format assay for a monovalent analyte (hapten) using a particulate direct label to reveal the assay result, in which assay the particulate label bears an antibody specific for the monovalent analyte and the detection zone of the strip contains immobilised analyte or an analogue thereof. Each label particle carries a multiplicity of identical antibody molecules. As a reagent, the antibody-bearing particles can be standardised during manufacture (ie. during application of antibodies to the particles) to ensure that within a given batch the loading of active antibody is constant. The concentration of analyte or analyte analogue in the detection zone should be in excess of the effective concentration (molar concentration) of antibody on the particles. It is not essential to have a constant antibody loading on each particle, because the number of particles can be varied. The quantity of particle-labelled antibody available in the assay should be in excess, relative to the anticipate analyte concentration in the sample. These levels can be adjusted by experimentation so that the presence of free analyte in the sample liquid leads to a significant level of binding of the free analyte to the antibodies on the particles and therefore significantly inhibits the possible binding of the particle label to the immobilised analyte/analogue in the detection zone. The principle behind this type of assay is that on the average particle there is a sufficient number of active antibody molecules to ensure binding of the particle in the detection zone, but that nevertheless the presence of analyte in the sample has a limiting effect on this binding. The extent to which the particles become bound in the detection zone is therefore inversely proportional to the concentration of analyte in the sample liquid. In a strip-format assay, the particle labelled antibody is placed upstream from the detection zone so that applied liquid sample encounters the particle labelled material and carries it to the detection zone. In this assay configuration it is necessary to ensure that the potential reaction between the free analyte and the particle-labelled antibody is at least substantially complete before these reagents reach the detection zone. The extent to which the particles bind to the immobilised analyte/analogue in the detection zone is therefore dependent on the residual uncomplexed antibody remaining on the particles. It is necessary to ensure that the concentration of immobilised analyte/analogue in the detection zone is high, to promote efficient capture of the particles as they pass through this zone. In order to enhance the efficiency of the previous binding of the particle-labelled antibody to free analyte in the sample liquid, it is very desirable that the antibody on the particles should have a very high affinity for the analyte. This affinity is preferably at least about $10^9$, and more preferably at least about $10^{10}$, litres/mole. The use of such high affinity antibodies ensures efficient capture of the free analyte by the particles, and moreover ensures that under assay conditions, once an analyte molecule has become bound to an antibody on the particle, it is very unlikely to be released or interchanged with an immobilised analyte/analogue molecule as the particle passes through the detection zone. These general principles apply also in an assay which is intended to determine two or more analytes, at least one of them being monovalent.

Hence, a preferred context in which the present invention is employed is an assay device for use in a method of determining the presence and/or concentration of two or more analytes in a single sample liquid, such as a urine sample, at least one of said analytes being determinable by means of a sandwich-format binding reaction involving two binding reagents specific for different epitopes on said analyte and at least one other of said analytes being a hapten (and therefore not determinable readily by means of a sandwich-format binding reaction), which method comprises the steps of:

a) providing a device comprising a strip of porous material along which said sample liquid can migrate, the strip having two or more spacially distinct detection zones (at least one per analyte to be determined) located downstream from the site of sample liquid addition to said strip, of which zones:

i) at least one zone contains an immobilised capture agent being a specific binding agent for said first analyte or a specific binding agent which can capture a sandwich-format complex including said first analyte, and ii) at least one other zone contains an immobilised capture agent which is either the hapten or an analogue thereof;

b) providing two or more populations of particles capable of migrating through said strip with said sample liquid, of which populations:

i) at least one population carries a binding agent specific for said first analyte, or specific for another specific binding agent which can participate in a sandwich-format reaction with said first analyte, and ii) at least one population other carries a binding agent specific for said hapten; and c) causing said populations of particles to become suspended in said sample liquid and to migrate with said sample liquid through said strip; the presence of said first analyte in said sample liquid leading to binding of particles in said at least one detection zone in an amount directly proportional to the concentration of said first analyte in said sample liquid, and the presence of said hapten in said sample liquid leading to a reduction in binding of particles of said at least one other population in said other detection zone in an amount directly proportional to the concentration of said hapten in said sample liquid, the detection zone containing the immobilised hapten or immobilised hapten analogue being preferably sited downstream from the detection zone associated with the first analyte.

An example of the first analyte is luteinizing hormone (LH). An example of the second analyte is estradiol or a metabolite thereof, such as estrone-3-glucuronide (E3G).

Preferably the particles are latex particles, which may be coloured.

Most preferably the affinity of the anti-hapten specific binding agent is at least about $10^9$, preferably about $10^{10}$, litres/mole.

Preferably the extent of particle binding in each of said detection zones is determined by measuring the extinction of electromagnetic radiation, such as light, when transmitted through the thickness of said strip.

The liquid flow-focussing wick of present invention is usefully applied in an assay device for use in the determination of two or more analytes in a single sample liquid, at least one of said analytes being determinable by means of a sandwich-format binding reaction involving two binding reagents specific for different epitopes on said analyte and at least one other of said analytes being a hapten (and therefore not determinable readily by means of a sandwich-format binding reaction), the device comprising, preferably within a protective casing:

a) a strip of porous material along which sample liquid can migrate;

b) two or more detection zones (at least one per analyte to be determined) on said strip, located downstream from the site of sample liquid addition to said strip, of which zones:

i) at least one zone contains an immobilised capture agent being a specific binding agent for said first analyte or a specific binding agent which can capture a sandwich format complex including said-first analyte, and ii) at least one other zone contains an immobilised capture agent which is either the hapten or an analogue thereof;

c) two or more populations of particles, located upstream from said detection zones, capable of migrating through said strip with said sample liquid, of which populations:

i) at least one population carries a binding agent specific for said first analyte, or specific for another specific binding agent also present in the device and which an participate in a sandwich-format reaction with said first analyte, and ii) at least one other population carries a binding agent specific for said hapten; the presence of said first analyte in said sample liquid leading to binding of particles in said at least one detection zone in an amount directly proportional to the concentration of said first analyte in said sample liquid, and the presence of said hapten in said sample liquid leading to a reduction in binding of particles of said at least one other population in said other detection zone in an amount directly proportional to the concentration of said hapten in said sample liquid, the detection zone containing the immobilised hapten or immobilised hapten analogue being preferably sited downstream from the detection zone associated with the first analyte.

Preferably the strip material is at least translucent through its thickness. An ideal strip material is nitrocellulose.

In this specific context, because the assay for the hapten is not a competition reaction in which there is the possibility of free interchange between analyte in the sample and analyte provided as a reagent in the assay (in this case the analyte/analogue immobilised on the strip) it is essential that during the course of the assay sufficient opportunity is provided for the analyte in the sample to become bound to the antibody bearing particles before these particles encounter the relevant detection zone on the strip. To ensure this it is desirable that there is a comparatively long contact time between the particulate reagent and the sample. Accordingly within the limits of acceptable physical geometry of the assay device the detection zone containing the immobilised analyte/analogue should be as far downstream from the source of the particle labelled reagent as possible. In particular, where the assay device is intended to determine two or more analytes in the same sample liquid and at least one of the other analytes is determined by means of a sandwich-format reaction, the detection zone for the hapten should ideally be downstream from the detection zone or zones involved in the sandwich-format assays.

A particular context of the invention is therefore a dual analyte strip format assay for determining LH and E3G in an applied urine sample in which the two assay results are detected in spacially distinct detection zones on the strip and the E3G zone is downstream from the LH detection zone relative to the site of sample liquid application, with the sample being received by a flow-focussing wick.

In one context, the invention is applied in a quantitative strip-format assay in which the assay result is revealed by binding in a detection zone a labelled reagent possessing multiple active binding sites specific for the analyte under test. The label is a detectable micro-particle, such as a (coloured) latex particle, metallic (e.g. gold) sold, dye sol, or non-metallic elemental (e.g. carbon, selenium) particle, of a size sufficiently small to permit migration through the porous strip material but sufficiently large to permit the formation of a detectable end-result when the labelled material is concentrated in the detection zone. Particulate labels of the types already used in stripformat sandwich assays are ideal. In a typical assay, the multiple active specific binding sites in the labelled reagent are provided by having a multiplicity of identical antibodies, preferably monospecific (eg monoclonal) antibodies, attached to each label particle.

According to EP 703454, especially in a hapten assay the use of particulate labels possessing multiple identical active analyte-specific binding sites leads to a valuable increase in sensitivity. The excess binding sites on the label particle allows effective binding of the particle in the hapten-bearing detection zone. However, perhaps because of the geometry of the system, which may be visualised as a planar detection zone surface and a more-or-less spherical label particle, the prior binding of merely a relatively small amount of hapten analyte from a sample to the curved surface of the label particle causes a degree of inhibition of binding of the label particle in the detection zone sufficient to influence the binding and cause a detectable effect.

It is highly desirable that once an analyte molecule has become specifically bound to the label particle, it should remain so bound throughout the remainder of the assay protocol leading to the formation of the detectable assay result in the detection zone. One way of achieving this is by using a specific binding agent in the labelled reagent which has a very high affinity for the analyte. It is now conventional to use monoclonal antibodies having analyte-affinities of $10^8$. We have found it advantageous to use, in the context of a strip-format hapten assay, labelled specific binding agents having analyte-affinities of at least about $10^9$ and more preferably of at least about $10^{10}$, litres/moles. A good method for measuring affinity in solution is described in Friguet et al, *J. Immunol Methods*, Vol 77 (1985) pages 305–319. Monoclonal antibodies having such high affinities can be raised in the conventional manner and identified by normal selection procedures. Although it is desirable to use antibodies which exhibit high affinity in solution, this is not the only way of achieving this. It is occasionally observed that an antibody that exhibits comparatively low affinity in solution can be transformed in its effective properties when immobilised on a solid phase.

An important embodiment of the invention is a quantitative strip-format assay for human body fluid analytes, especially haptens, using focused liquid flow as described herein. A particular example is such an assay for estradiol or a metabolite thereof, such as estrone-3-glucuronide (E3G). An especially important embodiment of the invention is a strip-format assay for urinary E3G which is capable of quantitatively determining the E3G over a concentration range of 5–60 ng/ml urine. Such an assay is particularly well suited for use in a procedure intended to provide a user with an awareness of the fertility status of an ovulation cycle, the body fluid concentration of estradiol or a metabolite thereof being recognised as a useful indicator of such status.

If desired, an assay device according to the invention, as set forth above, can additionally include the ability to determine other analytes in the same sample, if appropriate by employing conventional sandwich assay technology. For example, one embodiment of the invention is a strip-format assay device which can provide a quantitative determination of urinary E3G, as set forth above, and simultaneously a quantitative determination of urinary luteinizing hormone (LH) by means of a sandwich assay procedure, the E3G and LH results being revealed in two separate detection zones. Conveniently, in such a combined assay, the label can be the same for each assay, although the skilled reader will of course appreciate that two populations of label particles would normally be required, one carrying multiple binding sites for the E3G and the other carrying a specific binding material for the LH. The E3G detection zone will contain immobilised E3G or an analogue thereof, and the LH detection zone will contain immobilised specific binding material, such as an anti-LH antibody.

The invention will now be particularly described, by way of example only, with reference to the accompanying drawings which are not to scale.

DESCRIPTION OF THE DRAWINGS

FIGS. 7 and 8, corresponding to FIGS. 1 and 2, show an alternative construction of an assay device according to the invention.

DETAILED DESCRIPTION OF THE INVENTION

Figure 1:
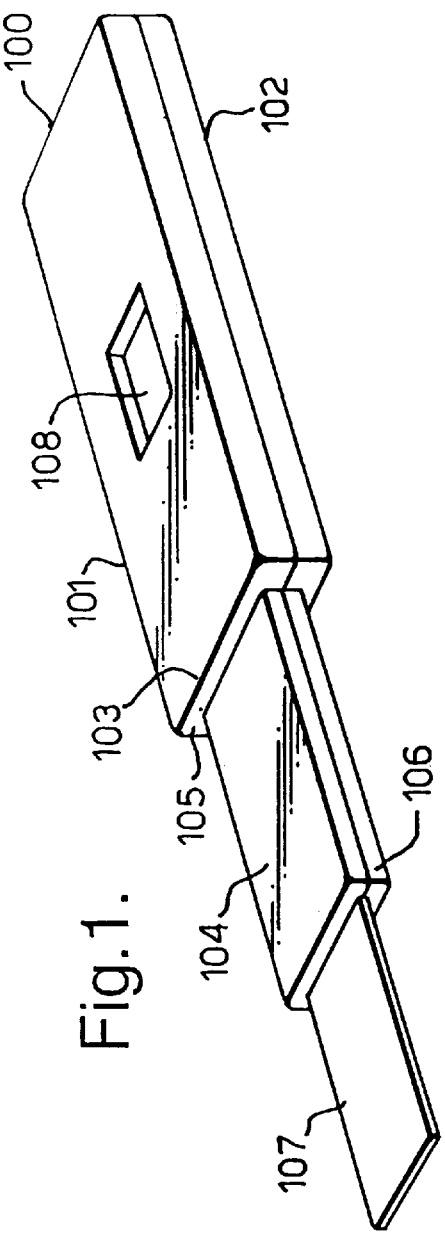
FIG. 1 is a general view of the exterior of an assay device.

Referring to FIG. 1, the assay device is of conventional external appearance and comprises a hollow casing 100 formed of upper and lower mouldings 101 and 102. Casing 100 is of generally rectangular elongate shape and at one end 103 has an extending portion 104 of narrower cross-section onto which a removeable cap (not shown) can be applied if desired. In a typical assay device, the cap would abut against shoulder 105 and when in place, provide a smooth continuous exterior to the whole device. From the forward end 106 of extended portion 104 of the casing projects a porous sample receiving member or wick 107 which acts to receive sample liquid and then convey the received liquid by capillary action into the interior of casing 100 as part of the intended liquid flow path. As seen in FIG. 1, upper moulding 101 of the casing includes a window 108 in its upper surface 109 through which the interior of the casing can be viewed. Window 108 enables a user to see the assay result which will be revealed as a visible colour change or similar effect which can be observed through the window. Alternatively the assay result can be read with the aid of an external reading instrument (not shown), such as by optical reflectance or optical transmission through the assay device. In the latter instance it is necessary for the underside of the assay device also to have a window or similar means through which light can be transmitted.

None of the details shown in FIG. 1 are critical to the invention, and considerable variation in the shape and external construction of the assay device can be made.

Figure 2:
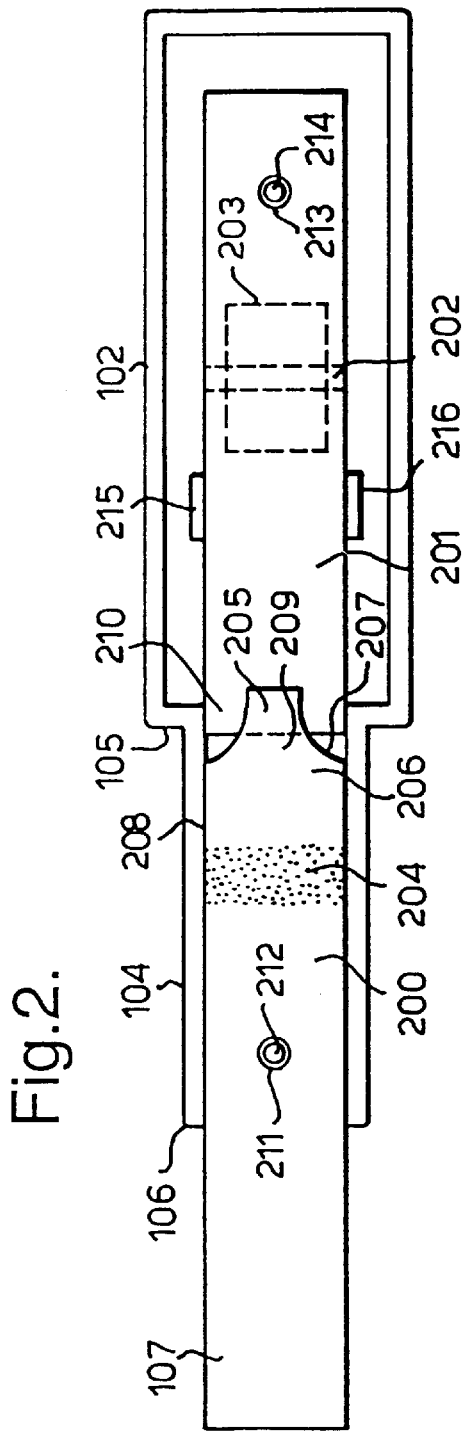
FIG. 2 is a plan view of the device of FIG. 1 with part of the device casing removed.

Referring to FIG. 2, the upper moulding has been removed to reveal the interior of the assay device. The essential internal components comprise the portion 200 of sample receiving member 107 which extends within the casing, and a further strip 201 of porous material which is in contact with sample receiving member 107 and includes a detection zone 202. The location of detection zone 202 is below the window in the upper casing moulding. The position of the window is indicated in broken lines 203.

The intended liquid flow path is along sample receiver 107 and from there along the length of porous strip 201 through and beyond detection zone 202. Within sample receiving member 107 at a location 204 hidden within the casing is deposited a supply of mobilisable labelled reagent which, in the moist state, is mobile within the sample receiver and the porous strip. Advancing sample liquid can pick up this mobilisable reagent and carry it towards the detection zone, in which the labelled reagent can accumulate and create an assay signal indicative of the test result. For example, the mobilisable reagent can be a specific binding reagent such as an antibody labelled with a visible label such as a particulate direct label. Examples are gold sols and coloured latex particles. Accumulation of the visible label in detection zone 202, for example by the formation of a sandwich complex with an analyte and a further specific binding agent already immobilised in the detection zone, leads to a build up of colour in the detection zone in a positive test.

At the interface 205 between sample receiving member 107 and porous strip 201 the lateral dimensions of the sample receiver are reduced so that the width of the sample receiver at that point is narrowed towards its centre line. This focusses the flow of the advancing liquid into the centre line of the porous strip, and thereby discourages advancing liquid from finding an alternative liquid flow path at the interface between the sample receiving member and the porous strip. The likelihood that the advancing liquid will flow elsewhere within the casing is thereby reduced.

As represented in FIG. 2, the sample receiver 107 is of generally elongate rectangular flattened shape. At its inner (right hand) end 206 each corner has been removed when the receiving member was cut or stamped into shape during manufacture. As shown, each corner has been removed to leave an inwardly curving edge 207 which runs from the side 208 of the sample receiver towards the extreme right hand end. These curving edges do not meet, but leave a protruding portion 209 of the sample receiver as a blunt point disposed on the centre line or longitudinal axis.

The interface between the sample receiving member 107 and the downstream porous strip 201 is created by an overlap between the protruding blunt point 209 and the upstream end 210 of the porous strip. Sample liquid advancing along the sample receiver is therefore focused into this blunt point before it reaches the interface with the porous strip, and thereby flows from the sample receiver into the porous strip. Once the sample liquid has entered the porous strip it is free to flow longitudinally and laterally therein, so that from the interface onwards the entire width of the porous strip can become moist. The dimensions of the porous strip can easily be chosen such that by the time the advancing liquid reaches the detection zone in the porous strip it is flowing substantially uniformly across through the entire width of the strip.

Sample receiving member 107 and porous strip 201 can be held in place within the casing by a variety of mechanisms. If desired, the sample receiving member and the porous strip can be linked together, for example, by being laminated onto a common backing strip (not shown) prior to insertion in the casing. Alternatively, or in addition, the sample receiving member and the porous strip can be held in place within the casing by physical constraints which form part of the casing moulding and which engage with the receiving member and strip. Purely by way of example only, one option is indicated in FIG. 2, wherein sample receiving member 107 is perforated by a hole 211 through which a pin 212 forming part of the lower device moulding protrudes when the receiving member is placed in the casing during assembly of the device. Similarly, porous strip 201 also has a perforation 213 through which another pin 214 protrudes. In addition to providing positive fixing locations for these components within the device casing, such perforations can also facilitate manufacture of the strip components (especially the accurate deposition of reagents) as is described in WO 95/13542. Other internal features of the casing moulding, such as lugs or ribs, can be present to provide additional or alternative locating means to hold the strip components in place. In FIG. 2, lugs 215 and 216 perform this function.

For the purposes of illustration, the assay device as shown in FIGS. 1 and 2 has been represented as being of very simple construction, with only two physical components making up the assay strip (sample receiver 107 and downstream porous strip 201) and only one detection zone 202. It is already common practice in the art for assay devices of this general type to be of much more complex construction. For example, it is common practice for the assay strip to contain a control zone, located usually downstream from the detection zone, in which a signal is revealed during use to reassure the user that the test has functioned properly. There may be more than one detection zone on the test strip, either to provide a quantitative result for a single analyte, or to provide simultaneous results for more than one analyte that may be present in the sample liquid. More than one mobile reagent may be provided, e.g. to provide specific results for different analytes or to provide different test and control signals. Where more than one mobile reagent is provided, these may start from a common point or be deposited at different points within the liquid flow path. It is unnecessary for the mobilisable reagent(s) to be located in the sample receiving member. Instead, such reagents can be located on the porous strip itself, upstream from the detection zone(s). Another alternative is the location of one or more mobilisable reagents in a further porous component which is located as an intermediate component between the sample receiving member and the strip containing the detection zone(s). In all of these options the benefits of the present invention can be realised if a flow focussing means as described is provided where the advancing liquid must traverse the interface from one porous component to the next.

Figure 3:
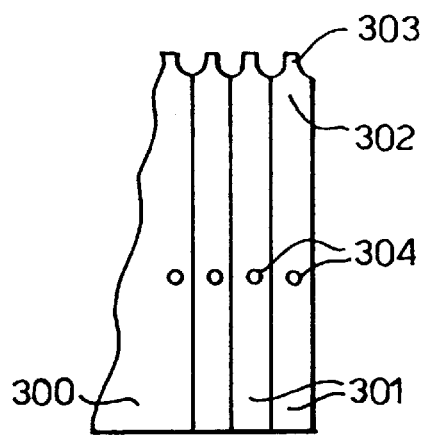
FIG. 3 depicts how an assay device wick in accordance with the invention can be cut from a larger sheet of porous material.

Referring to FIG. 3, a sheet or length 300 of material is being cut into individual sample receiving members (wicks) 301. During cutting, one end 302 of sample receiving member 301, which is intended to be the end within the device casing when assembled, is shaped to provide the liquid flow focussing means 303 in accordance with the invention. In FIG. 3 the liquid flow focussing portion 303 of the sample receiving member is created by two opposing inwardly-curving cuts which remove the corners of the sample receiver. Each wick is perforated by a hole 304 to provide a location means during assembly of the eventual assay device.

Figure 4:
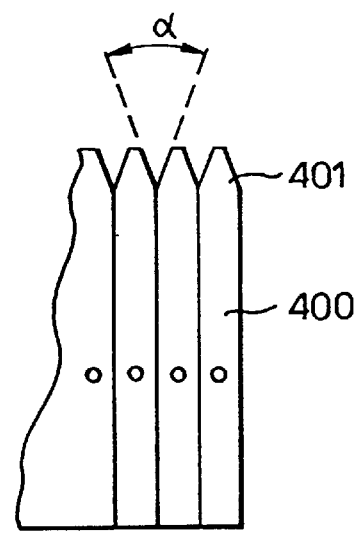
FIG. 4 depicts an alternative configuration to that seen in FIG. 3.

In FIG. 4, straight-line cuts are used to provide the sample receiver 400 with a blunt pointed end 401.

Figure 5:
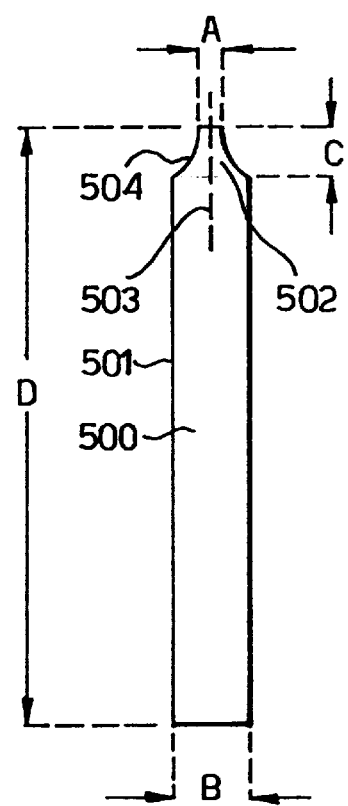
FIGS. 5 and 6 respectively show individual wicks formed as depicted in FIGS. 3 and 4.

FIG. 5 shows an individual wick 500 in accordance with the invention, as used in the device seen in FIG. 2. The wick is of substantially elongated rectangular form with parallel sides 501. However, the end 502 which is intended to be the downstream end when the wick is used as part of an assay device has a sharply progressively narrowed lateral dimension to provide the flow focussing characteristics critical to the invention. The resulting blunt point or prow of the wick is centred on the central longitudinal axis 503 of the rectangle. The sides 504 of this point or prow are concave curves. The width A of the extremity of the point or prow should be not greater than about 50% of the width B of the bulk of the wick. Preferably dimension A is not greater than about 40% of the dimension B. The dimension C which represents the portion of the length of the wick in which the width is sharply narrowed to provide the flow focussing characteristic should not be greater than about 35%, preferably not greater than about 25%, of the overall wick length D.

Ideally it is no greater than about 20% of D. In a typical wick in accordance with the invention, dimension D will lie in the range of about 2 to 10 cm, more usually from about 3 to about 7 cm, e.g. about 5 cm. Its width B will usually not exceed about 1 cm, and will typically be from about 5 to about 7 mm.

Figure 6:
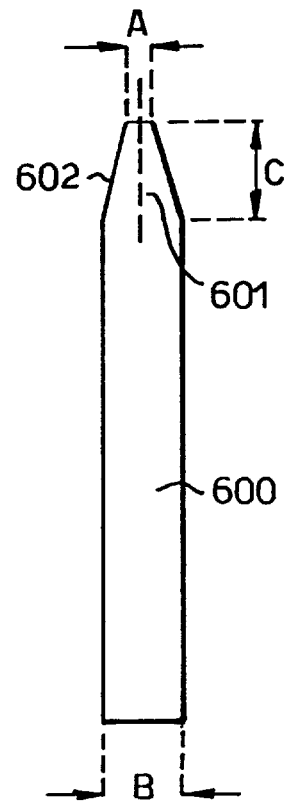

Referring to FIG. 6, a similar view is seen of a wick 600 having a point or prow 601 as generally depicted in FIG. 4, with straight inwardly-directed sides 602. The relative proportions A, B, C and D in the wick depicted in FIG. 6 should be determined according to the principles just described in respect of FIG. 5.

If desired, the point or prow of the wick can terminate in a true, ie. sharp, point, but a blunt point as described and illustrated herein is preferred.

FIGS. 7 and 8 show an alternative construction of an assay device in accordance with the invention, of similar basic concept to that already described above with reference to FIGS. 1 and 2.

FIG. 7 shows a general view of the exterior of the device. It comprises an elongated hollow casing 700 having a comparatively broad mid-portion 701 with narrower portions 702, 703 extending at each end. The casing is formed from an upper moulding 704 and a lower moulding 705, typically of plastics material. The forward extending portion 702 has a rounded end 706 incorporating a "mouth" 707 from which protrudes a porous sample receiving member (wick) 708. The rear portion 703 of the casing includes in its upper surface a rectangular window 709 revealing the inside of the device. There may be a corresponding window (not shown) on the underside of the device casing if it is desired that the test result is read by transmission through the device. The far end 710 of the casing terminates in a squared off shape having one bevelled corner 711. Optionally the device can be provided with a dual-location cap (not shown) as described in WO 95/13541.

Referring to FIG. 8, this shows the device of FIG. 7 with the upper casing moulding removed to reveal the internal components. [In this view the device is turned round in the informal drawings filed herewith.]

The sample receiving member (wick) 708 extends within the casing 705 to a distance beyond the far end 800 of the broadened casing portion 701. The far end 801 of wick 708 is sharply narrowed to provide a liquid flow focussing point or prow 802 as already described herein. Downstream from the wick is a second porous body 803 comprising a rectangular strip of carrier material, such as nitrocellulose. The prow 802 of the wick overlaps the forward end 804 of carrier 803 to provide liquid flow contact between these two components. Carrier strip 803 is retained in place by means of a perforation 805 which engages with a pin 806 moulded into the casing, and this is supplemented by other physical features of the device moulding represented by two lugs 807 and 808 which engage the sides 809, 810 of the carrier strip. The location of the wick is defined by a perforation 811 and corresponding moulded pin 812. Towards the downstream end 801 of the wick, but above the sharply narrowed portion 802, is a deposited band 813 of mobilisable reagent which, when the device is used, can be carried by a flowing sample liquid from the wick into the carrier material. The location of two reaction zones 814 and 815 are represented by broken lines on the carrier. These can be a test zone and (downstream) a control zone. Alternatively they can be distinct zones for detecting two different analytes in a common sample. In the latter instance the mobilisable reagent can comprise two distinct species which interact separately with the sample to provide signals in the two zones. Even more zones and reagents can be used in the device if desired. Where separate mobilisable reagents are included, it is not necessary for these to be deposited at the same location. The reaction zones 814 and 815 lie below the casing window, the position of which is indicated by broken lines 816.

In use, the presence of the prow at the far end of the wick focusses liquid flow towards the centre line of the carrier material and reduces the likelihood that at the interface between the two porous bodies the advancing liquid will deviate from the intended flow path.

The embodiment depicted in FIGS. 7 and 8 is an ideal test device for use in the measurement of the urinary concentration of hormones of relevance to the status of the human ovulation cycle. The wick is preferably formed from non-woven fabric as described herein. The mobilisable reagent preferably comprises two populations of particulate labels, such as latex particles, respectively bearing an anti-LH antibody and an anti-E3G antibody. One of the reaction zones (preferably the upstream zone) contains an immobilised specific binding reagent which can lead to capture of the labelled anti-LH antibody in the presence of LH analyte. The other reaction zone preferably contains an immobilised specific binding reagent which can lead to a competition reaction when E3G is present in the applied sample. In the preferred embodiment the upstream detection zone produces a detectable signal which is directly proportional to the concentration of LH in the applied sample. The downstream zone produces a detectable signal that is inversely proportional to the concentration of E3G. The intensity of signals generated in these zones can be read optically, preferably by transmission through the device. The signals can be interpreted by means of an electronic monitor. The flow focussing properties of the shaped wick of the invention contribute to the sensitivity of the assay and therefore the accuracy of information derived therefrom.

By providing the porous body, eg. the sample receiving member, with a sharply narrowed extremity at the interface with the downstream porous body, the invention provides liquid flow focussing advantages without diminishing any of the other attributes of the porous component. For example, in the case of the sample receiving member, it is desirable that this member should have maximum liquid absorbing capacity to provide an adequate reservoir of sample liquid to drive the assay device. It would therefore be very undesirable to have the sample receiving member of substantially narrower width throughout its entire length. Although having the sample receiving member of narrower width than its downstream partner might provide some liquid focussing benefit at the interface, the additional length of the narrow sample receiving member necessary to provide comparable liquid holding capacity would be undesirable. This would increase the overall dimensions of the assay device and render it less easy to use and to manufacture. There is a desire within the art to make tests of this type operate in the minimum of time, and this objective is inconsistent with increasing the total length of the liquid flow path.

A further benefit of the liquid flow focussing wick of the invention is that its use in an assay device can lead to enhanced assay sensitivity.

A yet further benefit of the specially-shaped wick is that much greater manufacturing tolerances are provided during assembly of an assay device. If the wick is misaligned during assembly of a device comprising a casing and a series of porous components, unnecessary contact may be created between the wick and the interior of the casing. By the use of a flow-focussing wick in accordance with the invention, slight misalignment of the downstream end of the wick can be tolerated without leading to a situation in which flooding of the assay device may arise at the interface between the wick and the next porous component.

What is claimed is:

1. An assay device incorporating a composite strip comprising at least two bodies of porous liquid-conductive material so as to provide an upstream body and a downstream body in liquid-flow contact with each other via an interface and together defining at least part of a liquid flow path through which liquid must flow during the performance of an assay, wherein at said interface the lateral dimension, relative to the direction of said liquid flow path, of the contact area of the upstream body is narrowed such that liquid flow from said upstream body into the downstream body is focused towards the centre-line of said flow path in said downstream body, the upstream body being narrowed at said interface by at least 50% of its width to provide a narrowed point or prow on the centre-line of said flow path for contact with said downstream body, said narrowed point or prow of the upstream body overlapping with the downstream body to provide the interface for contact between the upstream body and said downstream body whereby deviation from the intended flow path is reduced.

2. An assay device according to claim 1, wherein said upstream body incorporates a mobilisable reagent upstream from said narrowed portion of said porous body.

3. An assay device according to claim 1, which can detect the presence or concentration of at least two different analytes in a single sample applied to said assay device.

4. An assay device according to claim 3, which can detect in a single applied urine sample both E3G and LH.

5. An assay device according to claim 1, wherein said bodies of porous material are contained at least partially within a hollow casing constructed of solid moisture-impervious material.

6. An assay device according to claim 1 or claim 5, wherein said bodies of porous material are physically separate components and are placed in contact with one another during assembly of said device.

7. An assay device according to claim 5, wherein said bodies of porous material are physically separate components and are held in contact with one another solely by being constrained within said hollow casing.

8. An assay device according to any claim 1, wherein said upstream body is a sample receiving member or wick.

9. An assay device according to claim 8, wherein said bodies of porous material are contained at least partially within a hollow casing constructed of solid moisture-impervious material, and said sample receiving member or wick protrudes from said casing but the portion of said sample receiving member or wick which is narrowed is within said casing.

10. An assay device according to claim 8 or claim 9, wherein said sample receiving member or wick is made from non-woven fabric.

11. An assay device according to claim 8 or claim 9, wherein said sample receiving member or wick is made from fibrous plastics material.

12. An assay device, according to claim 9 wherein said wick comprises a strip of porous material having at one end thereof a narrowed point or prow centred on the longitudinal axis of said strip.

13. An assay device according to claim 12, in which said narrowed portion extends over not more than 35% of the overall length of said wick.

14. An assay device incorporating a composite strip comprising at least two bodies of porous liquid-conductive material in liquid-flow contact with each other via an interface and together defining at least part of a liquid flow path through which liquid must flow during the performance of an assay, wherein at said interface the lateral dimension, relative to the direction of said liquid flow path, of the contact area of the upstream body is narrowed such that liquid flow from said upstream body into the downstream body is focused towards the centre-line of said flow path in said downstream body, both said upstream and downstream bodies including reagents for said assay, the upstream body incorporating a mobilizable reagent upstream from said narrowed portion, the narrowed area of the upstream body overlapping with the downstream body to provide the interface for contact between the upstream body and said downstream body whereby deviation from the intended flow path is reduced.

* * * * *